United States Patent
Wang et al.

(10) Patent No.: US 9,758,450 B2
(45) Date of Patent: Sep. 12, 2017

(54) INTEGRATED PROCESS TO PRODUCE 2,3,3,3-TETRAFLUOROPROPENE

(71) Applicant: HONEYWELL INTERNATIONAL INC., Morristown, NJ (US)

(72) Inventors: Haiyou Wang, Amherst, NY (US); Selma Bektesevic, Williamsville, NY (US); Daniel C. Merkel, Orchard Park, NY (US); Hsueh Sung Tung, Getzville, NY (US); Konstantin A. Pokrovski, Orchard Park, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 15/093,970

(22) Filed: Apr. 8, 2016

(65) Prior Publication Data

US 2016/0221898 A1 Aug. 4, 2016

Related U.S. Application Data

(63) Continuation of application No. 14/204,131, filed on Mar. 11, 2014, now Pat. No. 9,334,206.

(60) Provisional application No. 61/792,980, filed on Mar. 15, 2013.

(51) Int. Cl.

| | | |
|---|---|---|
| *C07C 17/38* | (2006.01) | |
| *C07C 17/386* | (2006.01) | |
| *C07C 17/383* | (2006.01) | |
| *C07C 17/25* | (2006.01) | |
| *C07C 17/20* | (2006.01) | |
| *C07C 21/18* | (2006.01) | |
| *C07C 17/087* | (2006.01) | |
| *C07C 21/04* | (2006.01) | |
| *C07C 19/01* | (2006.01) | |
| *C07C 19/08* | (2006.01) | |
| *C07C 19/10* | (2006.01) | |

(52) U.S. Cl.
CPC .......... *C07C 17/206* (2013.01); *C07C 17/087* (2013.01); *C07C 17/25* (2013.01); *C07C 17/38* (2013.01); *C07C 17/386* (2013.01); *C07C 21/18* (2013.01); *C07C 19/01* (2013.01); *C07C 19/08* (2013.01); *C07C 19/10* (2013.01); *C07C 21/04* (2013.01); *Y02P 20/125* (2015.11); *Y02P 20/582* (2015.11)

(58) Field of Classification Search
CPC ........ C07C 17/25; C07C 17/20; C07C 17/206; C07C 17/38; C07C 17/383
See application file for complete search history.

(56) References Cited

U.S. PATENT DOCUMENTS

| | | | |
|---|---|---|---|
| 6,013,846 A | 1/2000 | Wismer et al. | |
| 7,183,448 B2 | 2/2007 | Nakada et al. | |
| 8,034,251 B2 | 10/2011 | Merkel et al. | |
| 8,058,486 B2 | 11/2011 | Merkel et al. | |
| 8,084,653 B2 | 12/2011 | Tung et al. | |
| 8,114,308 B2 | 2/2012 | Merkel et al. | |
| 8,168,837 B2 | 5/2012 | Merkel et al. | |
| 8,207,383 B2 | 6/2012 | Deur-Bert et al. | |
| 2007/0197842 A1* | 8/2007 | Mukhopadhyay | C07C 17/00 570/155 |
| 2009/0224207 A1* | 9/2009 | Pham | C07C 17/38 252/372 |
| 2009/0227822 A1 | 9/2009 | Pham et al. | |
| 2009/0240090 A1 | 9/2009 | Merkel et al. | |
| 2011/0105807 A1* | 5/2011 | Kopkalli | C01B 7/0718 570/155 |
| 2012/0010449 A1 | 1/2012 | Wismer et al. | |
| 2012/0203037 A1 | 8/2012 | Sharratt et al. | |
| 2012/0296128 A1 | 11/2012 | Merkel et al. | |
| 2013/0041191 A1 | 2/2013 | Pigamo | |

FOREIGN PATENT DOCUMENTS

| | | |
|---|---|---|
| CN | 102001910 A | 4/2011 |
| WO | WO2012075283 A2 | 6/2012 |

OTHER PUBLICATIONS

First Office Action issued in Chinese Application No. 201480016030.X issued May 3, 2016 (in English and Chinese).
Supplementary European Search Report issued in Application No. 14 76 7769 dated Oct. 7, 2016.

* cited by examiner

*Primary Examiner* — Medhanit Bahta
(74) *Attorney, Agent, or Firm* — Scully Scott Murphy and Presser

(57) ABSTRACT

The invention relates to a separation process whereby 2-chloro-3,3,3-trifluoropropene (1233xf) is separated from a mixture containing other fluorinated organics and high boiling materials such as dimers using azeotropes of HF formed by adding appropriate amounts to the mixture which facilitate separation by, e.g. distillation.

18 Claims, No Drawings

INTEGRATED PROCESS TO PRODUCE 2,3,3,3-TETRAFLUOROPROPENE

This application is a continuation application claiming priority under 35 USC 120 to U.S. Ser. No. 14/204,131 filed Mar. 11, 2014, a notice of allowance in which issued on Jan. 8, 2016, which claims priority under 35 USC 119 to provisional application U.S. Ser. No. 61/792,980 filed Mar. 15, 2013.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Certain hydrofluoroolefins (HFOs), such as tetrafluoropropenes (including 2,3,3,3-tetrafluoropropene (HFO-1234yf)), are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike most chlorofluorocarbons (CFCs) and hydrochlorofluorocarbons (HCFCs), most HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf is a leader among the materials being developed for use in many of the aforementioned applications.

A manufacturing process for HFO-1234yf, as e.g. disclosed in U.S. Pat. No. 8,058,486, uses 1,1,2,3-tetrachloropropene (HCO-1230xa) as starting raw material. The process consists of the following three steps: (1) HCO-1230xa+HF→2-chloro-3,3,3-trifluoropropene (HCFO-1233xf)+HCl in a vapor phase reactor charged with a solid fluorination catalyst, (2) HCFO-1233xf+HF→2-chloro-1,1,1,2-tetrafluoropropane (HCFC-244bb) in a liquid phase reactor charged with a liquid hydrofluorination catalyst, and (3) HCFC-244bb→HFO-1234yf in a vapor phase reactor.

As also disclosed in U.S. Pat. No. 8,058,486, subsequent to Step (1) above, the effluent stream exiting the vapor phase reactor is fed to a first recycle column. The lighter components, including HCl, HCFO-1233xf, HCFC-244bb, HFC-245cb, and small amounts of HF, are isolated as a top light stream, and are fed to next unit operation as a crude first intermediate stream. The majority of the un-reacted HF and heavy intermediates are isolated as a bottom heavy stream, and are fed back to the vapor phase reactor of Step (1). Nevertheless, high boilers such as 1230xa dimers, e.g. $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and the like, are also included in this bottom heavy stream that is sent to the vapor phase reactor, where such materials can cause the deactivation of catalyst.

As disclosed in U.S. Provisional Patent Application No. 61/604,629, filed Feb. 29, 2012, in an improved integrated process, a phase separator is used to receive the said bottom heavy stream so as to concentrate these non-recyclable high boilers. While the 1233xf contained in the HF phase of the separator is recycled back to the Step (1) reactor together with HF, substantial amounts of 1233xf and other recyclable byproducts such as 1232xf, 243 isomers, etc. are still present in the organic phase, together with non-recyclable high boilers. Due to the presence of high boilers, it is difficult to further isolate recyclable species using conventional distillation method. Hence, there is a need for means by which 1233xf and other recyclable byproducts can be efficiently recovered.

SUMMARY OF THE INVENTION

The present invention relates, in part, to one or more process steps for improving the reaction efficiency used for the production of HFOs, such as 2,3,3,3-tetrafluoropropene (1234yf).

In one aspect, the present invention relates to a process for preparing 2-chloro-3,3,3-trifluoropropene by providing a starting composition including at least one compound of formula I, II, and/or III $$CX_2=CCl-CH_2X \qquad (I)$$

$$CX_3-CCl=CH_2 \qquad (II)$$

$$CX_3-CHCl-CH_2X \qquad (III)$$

wherein X is independently selected from F, Cl, Br, and I, provided that at least one X is not fluorine. Such a starting composition is contacted with a fluorinating agent, such as HF, to produce a final composition including 2-chloro-3,3,3-trifluoropropene (1233xf), HCl, unreacted HF, optional unreacted starting compound(s), and one or more by-products. The by-products may include, without limitation, one or a combination of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243) isomers, trichlorodifluoropropane (242) isomers, and dimer(s) such as $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and the like. In certain aspects, at least one of the compounds is recyclable back to the contacting step.

This final composition is then processed to separate desired products and recyclables from the remainder of the final composition. In one aspect, 1233xf and HCl are first separated by feeding the composition into a recycle or distillation column. From such a column, the lighter components, such as 1233xf, 244bb (if any), 245cb (if any), HCl, and a portion of unreacted HF are isolated in a first or top stream, and the remaining components, such as unreacted HF, optional unreacted starting compounds, one or more by-products, and residual 1233xf are recovered in a second or bottom stream. From this first or top stream, 1233xf is purified using standard distillation methods, such as those provided herein. It, the 1233xf, is then forwarded to the second step of the reaction (discussed below) to produce 244bb and, ultimately, 1234yf.

The bottom stream of the recycle or distillation column is then further processed to isolate recyclable compounds from Step (1) of the reaction aforesaid. Unreacted HF, for example, is substantially separated by phase separation. More specifically, the second or bottom stream from the recycle column is provided to a phase separator where unreacted HF separates into a first layer (or HF-rich layer). In certain embodiments, this first layer also includes, as a residual portion, certain of the organics such as, but not limited to, 1233xf, 1232xf, and 243. The remaining organics (e.g. optional unreacted starting compound, residual 1233xf, and one or more by-products, which may include 1231, 1232xf, 243, 242, and various dimers, are separated into a second layer (or organic-rich layer). The HF-rich first layer is then extracted, optionally purified, and recycled.

The organic-rich layer of the phase separator may be similarly extracted and further processed to recover the unreacted starting material (if any), residual 1233xf, and other recyclable by-products such as 1231, 1232xf, 243, 242, and the like for recycling. In one aspect, the extracted organic-rich stream is sent to a distillation column for processing. In a preferred embodiment, to better recover the unreacted starting material (if any), 1233xf and other recyclable by-products, HF is added to the mixture during distillation in an amount sufficient to form various binary and/or ternary azeotropic or azeotrope-like compositions with hydrogen fluoride, and thereafter the azeotropic or azeotrope-like compositions are separated from high boiling point non-recyclable by-products such as dimers. Non-limiting examples of azeotropic or azeotrope-like compositions include 1230xa/HF, 1233xf/HF, 1232xf/HF, 244bb/HF, 243db/HF, 1233xf/244bb/HF, etc.

The instant invention relates to the finding that the addition of HF to the extracted organic-rich stream from the phase separator provides for easier recovery of 1233xf and other recyclable by-products. The economy of the process is therefore improved. Additional embodiments and advantages to the present invention will be readily apparent to one of skill in the art, based on the disclosure provided herein.

In one embodiment, the invention relates to a separation process which comprises:
providing a first composition comprising i) 2-chloro-3,3,3-trifluoropropene (1233xf), ii) one or more organics selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243) isomers, trichlorodifluorpropane (242) isomers, and optionally iii) one or more dimers selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$;
adding HF to said first composition in an amount effective to form a second composition comprising HF-azeotropes of 1233xf and of at least one of the organics;
separating at least a portion of the HF-azeotropes from the second composition.

In one embodiment, the invention relates a process to prepare 2-chloro-3,3,3-trifluoropropene (1233xf) comprising providing a starting composition comprising at least one starting compound of formula I, II and/or formula III

$$CX_2=CCl—CH_2X \qquad (I)$$

$$CX_3—CCl=CH_2 \qquad (II)$$

$$CX_3—CHCl—CH_2X \qquad (III)$$

wherein X is independently selected from F, Cl, Br, and I, provided that at least one X is not fluorine;
(a) contacting said starting composition with a fluorinating agent under conditions effective to produce a first composition comprising 1233xf, unreacted fluorinating agent, HCl, optionally unreacted starting compound, and one or more organics selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243) isomers, trichlorodifluorpropane (242) isomers, and optionally one or more dimers selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof;
(b) separating, from the first composition, a second composition comprised of an amount of 1233xf and substantially all of said organics and optionally dimers;
(c) adding HF to the second composition in an amount effective to form a third composition comprising HF-azeotropes of 1233xf and at least one of the organics, said second composition further comprising the optional dimers;
(d) separating the HF-azeotropes from the third composition; and
(e) recovering 1233xf from the HF-azeotropes separated in step (d).

The 1233xf that is separated using the invention can be recycled and otherwise used in processes to make materials such as 244bb and 1234yf.

DETAILED DESCRIPTION OF THE INVENTION

The foregoing general description and summary and the following detailed description are exemplary only and are not restrictive of the invention as defined in the appended claims. Other features and benefits of any of the embodiments herein will be apparent from the present disclosure. The entire contents of U.S. Pat. No. 8,084,653 and US Published Patent Application 2009/0240090 are incorporated herein by reference.

According to one embodiment, the present invention relates to a manufacturing process for making 2,3,3,3-tetrafluoroprop-1-ene using a starting material according to any one or combination of Formulas I, II, and/or III:

$$CX_2=CCl—CH_2X \qquad \text{(Formula I)}$$

$$CX_3—CCl=CH_2 \qquad \text{(Formula II)}$$

$$CX_3—CHCl—CH_2X \qquad \text{(Formula III)}$$

wherein X is independently selected from F, Cl, Br, and I, provided that at least one X is not fluorine. In certain embodiments, the compound(s) of Formula I, II and/or III contains at least one chlorine, a majority of the Xs as chlorine, or all Xs as chlorine. In certain embodiments, the compound(s) of Formula I includes 1,1,2,3-tetrachloropropene (1230xa). In certain embodiments, the compound(s) of Formula II includes 2,3,3,3-tetrachloropropene (1230xf). In further embodiments, the compound(s) of Formula III include 1,1,1,2,3-pentachloropropane (240db).

The method generally includes at least three reaction steps. In Step (1), a starting composition including compounds of Formula I, II, and/or III (e.g. 1,1,2,3-tetrachloropropene, 2,3,3,3-tetrachloropropene, and/or 1,1,1,2,3-pentachloropropane) is reacted with anhydrous HF in a first vapor phase reactor (fluorination reactor) under conditions effective to produce a mixture of 2-chloro-3,3,3-trifluoropropene (12334 and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated.

Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $COCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This Step (1) of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. If desired, inert gases such as nitrogen or argon may be employed in the reactor during operation.

When the compound of Formula I is 1230xa, the mol ratio of HF to 1230xa in Step (1) of the reaction is 1:1 to 50:1, from about 10:1 to about 50:1, or from about 10:1 to about 20:1. The reaction between HF and 1230xa is carried out at a temperature from about 200° C. to about 600° C., in certain embodiments, about 200° C. to about 400° C., or about 200° C. to about 300° C. The reaction pressure is about of about 0 psig to about 500 psig, in certain embodiments from about 20 psig to about 200 psig, or about 50 to about 100 psig.

Similarly, when the compound of Formula II is 1230xf, the mol ratio of HF to 1230xf in step 1 of the reaction is 1:1 to 50:1, from about 10:1 to about 50:1, or from about 10:1 to about 20:1. The reaction between HF and 1230xf is carried out at a temperature from about 200° C. to about 600° C., in certain embodiments, about 200° C. to about 400° C., or about 200° C. to about 300° C. The reaction pressure is about of about 0 psig to about 500 psig, in certain embodiments from about 20 psig to about 200 psig, or about 50 to about 100 psig.

Similarly, when the compound of Formula III is 240db, the mol ratio of HF to 240db in step 1 of the reaction is 1:1 to 50:1, from about 10:1 to about 50:1, or from about 10:1 to about 20:1. The reaction between HF and 240db is carried out at a temperature from about 200° C. to about 600° C., in certain embodiments, about 200° C. to about 400° C., or about 200° C. to about 300° C. The reaction pressure is about of about 0 psig to about 500 psig, in certain embodiments from about 20 psig to about 200 psig, or about 50 to about 100 psig.

The fluorination reaction may be carried out to attain a single- or multi-pass conversion of at least 1% or higher, 5% or higher, 10% or higher or about 20% or higher. In certain preferred embodiments of the present invention, the starting reagent is converted to 1233xf in a single pass, wherein the reaction conditions achieve a conversion amount greater than 75%, greater than 85%, greater than 95% or greater than 99%. To this end, the resulting effluent includes small or trace amounts of unreacted starting material or may be substantially free of such compounds.

The effluent from the fluorination reaction step, Step (I), including any intermediate effluents that may be present in multi-stage reactor arrangements, are processed to achieve desired degrees of separation and/or other processing. For example, in embodiments in which the reactor effluent includes 1233xf, the effluent will generally also include HCl, unreacted HF, and trace amounts, if any, of unreacted starting component (e.g. 1230xa, 1230xf and/or 240db). The effluent may also include one or more by-product organics such as underfluorinated and/or overfluorinated intermediates. Non-limiting examples of underfluorinated intermediates include trichlorofluoropropene (1231) isomers and 2,3-dichloro-3,3-difluoropropene (1232xf), and non-limiting examples of overfluorinated intermediates include 2-chloro-1,1,1,2-tetrafluoropropane (244bb) and 1,1,1,2,2-pentafluoropropane (245cb). Other by-product organics may also include, but are not limited to, dichlorotrifluoropropane (243) isomers, and trichlorodifluoropropane (242) isomers, and dimers derived from one or more of the starting compounds. By way of non-limiting example, dimers derived from 1230xa include, but are not limited to, $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and the like.

The effluent from Step (1) may be processed in one or more steps to isolate the 1233xf, as well as certain unreacted components and/or byproducts that are useful as recyclables. In one embodiment, starting reagent is provided to a drier and then to the reactor along with HF. The effluent stream exiting the vapor phase reactor is fed to a cooler and then to a first recycle column, such as a distillation column. The lighter components of the effluent are isolated from the top of the first recycle column and cooled and include one or more of HCl, 1233xf, 244bb (if any), 245cb (if any) and a portion of unreacted HF. The remaining compounds are collected at the bottom stream of the column and include a bulk of the unreacted HF, trace amounts of unreacted starting component (if any), residual 1233xf and one or more of the by-product organics discussed herein. When referring to the bottom stream of the column, a "residual" amount of 1233xf refers to less than about 30 wt %, less than about 20%, less than about 15%, or less than about 10% of the total weight of the components in the bottom stream.

Each of the top stream and bottom stream are then independently processed. The top stream, for example, is first fed into an HCl column for HCl removal. High purity HCl is isolated from the top of the column and fed to an HCl recovery system. By way of non-limiting example, in such a recovery system HCl from the top stream may be absorbed in de-ionized water as concentrated HCl, which, optionally, can be recovered for later sale. The remaining components, including 1233xf, 244bb (if any), 245cb (if any), and HF, exit the bottom of the HCl column and are further processed. In certain embodiments, this bottom stream is then provided to an HF recovery system to recover HF. The 1233xf/HF stream is fed to a sulfuric acid extractor or a phase separator for removal of HF from this mixture, i.e. the HF is either dissolved in sulfuric acid or phase separated from the organic mixture. With the former, HF is desorbed from the sulfuric acid/HF mixture by heating and distillation and recycled back to the reactor. In the case where a phase separator is used, HF is phase-separated using standard methods, such as those discussed below, and recycled back to the reactor. The organic either from the overhead of the sulfuric acid extractor or from the bottom layer of the phase separator is fed to the hydrofluorination reactor of Step (2), discussed below.

Components within the bottom stream of the first recycle column are separated, in certain embodiments, by phase separation. More specifically, the mixture is provided to a cooler and then to a phase separator where unreacted HF separates into an HF-rich first or top layer and an organic-rich bottom or second layer. In one practice, separation is such that substantially all of the HF from the mixture is in the top layer, and substantially all of the organics and/or dimers from the mixture are in the bottom layer. "Substantially all" as used herein means more than half. Thus in the present context, "substantially all" means that more than half of the HF in the mixture is separated such that it is in top layer, and respectively, that more than half of the organics and/or dimers in the mixture are separated such that they are in the bottom layer. More than half includes those percentages from over 50% (e.g. over 50% of the HF from the mixture is separated into the top layer of the phase separation process) up to and including 100% and all intermediate values. The phrases "HF-rich" and "organic-rich" have the same quantitative meaning as "substantially all." Any pressure which maintains the mixture substantially in the liquid phase may be employed. To this end, the pressure and temperature of the mixture may be adjusted such that the mixture remains substantially in the liquid phase. In certain embodiments, the HF-rich layer also includes, as a residual portion, certain of the organics such as, but not limited to 1233xf, 1232xf and 243 isomers. The remaining organics not provided in the first layer (particularly unreacted starting compound(s) (if any), residual 1233xf, 242 isomers, 243 isomers and dimers) separate into the organic-rich second or bottom layer. (When referring to the top layer, a "residual portion" of organics refers to less than about 50 wt %, less than about 40%, less than about 30%, less than about 20%, or less than about 10% of the total weight of the components in the top layer.) Phase separation may be performed at any combination of temperature and pressure such that two distinct liquid phases are formed in the phase separator. Phase separation may be carried out between about −30° C. to 60° C., preferably between about 0° C. and 40° C. and more preferably between about 10° C. and 30° C.

The HF rich layer is then isolated, such as by HF phase pump, optionally purified, and recycled back to the reactor via vaporizer. In one embodiment, the HF-rich layer is distilled to remove any moisture buildup or is isolated by single stage flash distillation. In another embodiment, before the recycle of HF-rich stream moisture (if any) is removed by injecting a chemical reagent such as $COCl_2$ (or $SOCl_2$) into said stream, which reacts with moisture to form $CO_2$ (or $SO_2$) and HCl. In even further embodiments, the HF-rich layer may be purified to remove the residual organics or may be recycled with the organics.

The organic-rich layer is also isolated, such as by organic phase pump, then further processed to separate and purify the unreacted starting reactants (if any) and recyclable intermediates. In certain embodiments, the organic-rich layer is provided to a high boiler purge system, where unreacted starting reagents (if any), residual 1233xf, 1231 isomers, 1232xf, 243 isomers, 242 isomers, etc. are recovered and undesirable by-products, particularly dimers and other impurities, are removed. When referring to the organic-rich layer, a "residual" amount of HF refers to less than about 15 wt %, less than about 10%, less than about 5%, or less than about 3% of the total weight of the components in the bottom layer. Organics in this regard are, without limitation, those selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243) isomers, trichlorodifluorpropane (242) isomers, and the like.

The high boiler purge system may be a distillation system operated in batch or continuous mode, preferably batch for operational reasons. Another option is to use a flash or series of flashes. In either case (distillation or flash), the more volatile components are recovered and recycled while the heavier components are removed from the system. In one non-limiting embodiment, the organic-rich layer is isolated, such as by organic phase pump, and is provided to a batch distillation column for separation. The lighter components (e.g. unreacted starting compounds including HF, 1231 isomers, 1232xf, residual 1233xf, 242 isomers, and 243 isomers) are isolated from top stream(s). Non-condensable compounds (if any) are optionally purged and the lighter compounds are collected as a series of distillation cuts where compounds are separated in order of volatility. It is noted that any number of distillation cuts may be provided to separate the valuable or recyclable materials, e.g. unreacted starting compounds, 1231 isomers, 1232xf, 1233xf, 243 isomers, 242 isomers, etc. Once isolated, unreacted starting compounds, 1233xf, 1231 isomers, 1232xf, 243 isomers, 242 isomers may be recycled to the reactor of the first step. In doing so, the unreacted starting components (if any) and the recyclable intermediates are converted to the desired composition 1233xf and/or its precursors. The heavy compounds (e.g. dimers, etc.) are isolated from the bottom stream. Dimers in this regard include, without limitation, materials such those selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$ and the like.

In a preferred embodiment of the present invention, to better recover the unreacted starting material (if any), 1233xf and other recyclable by-products such as 1231 isomers, 1232xf, 243 isomers, 242 isomers, HF is added to the mixture during distillation in an amount effective to form HF-azeotropes of 1233xf and at least one of the organics, e.g. in an amount effective to form various binary and/or ternary azeotropic or azeotrope-like compositions of the organics with the hydrogen fluoride; thereafter the azeotropic or azeotrope-like compositions are separated from high boiling point non-recyclable by-products such as dimers including $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and the like. Non-limiting examples of azeotropic or azeotrope-like compositions include 1230xa/HF, 1233xf/HF, 1232xf/HF, 244bb/HF, 243db/HF, 1233xf/244bb/HF, etc.

The concentration of HF in the resultant mixture after HF addition can vary in a wide range from 5 to 95 wt %, preferably from 20 to 80 wt %, and more preferably from 30 to 70 wt %.

In one practice of the invention, the addition of HF to the extracted organic-rich stream from the phase separator allows for easier recovery of 1233xf and other recyclable by-products. The economy of the process is therefore improved.

Removal of the high boiling point by-products and impurities is advantageous because such compounds cause catalyst deactivation if recycled. During phase separation, as set forth above, such compounds tend to concentrate in organic layer. Accordingly, post-isolation, the organic layer can also be purified in accordance with the foregoing to remove such compounds and isolate only those compounds that are recyclable. Removal of the high boiling point compounds results in improved catalyst life and minimal purge streams.

In Step (2) of the aforementioned process for forming 2,3,3,3-tetrafluoroprop-1-ene, the purified 1233xf intermediate stream is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This Step (2) of the reaction whereby 244bb product is formed is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

The effluent from the hydrofluorination reaction step, Step (2), which consists mainly of 244bb and HF (plus small amounts of unreacted 1233xf, overfluorinated by-product 245cb, HCl, and $Cl_2$), is processed to achieve desired degrees of separation and/or other processing. For example, the product stream is fed to a lights removal column where a stream consisting of mainly 245cb, HCl, and $Cl_2$ exits the top of the column and is sent to a thermal-oxidizer (T-OX) for destruction. In one practice, the lights removal column bottom stream consisting of mainly 244bb and HF (plus a small amount of unreacted 1233xf) is fed into a phase separator for HF recovery. The HF rich top layer is recycled back to the Step (2) reactor. The organic rich bottom layer containing mainly 244bb (plus small amounts of HF and 1233xf) is sent forward, together with an HF stream, to a distillation column for separation. The concentration of HF in the resulting mixture, in an embodiment, is between about 0.01% by weight to about 20% by weight; in another embodiment, the concentration HF is between about 0.05% to about 10% by weight; in another embodiment, the concentration of HF is between about 1% by weight to about 6% by weight; in another embodiment, the concentration of HF is between about 2% by weight to about 4% by weight; in another embodiment, the concentration of HF is about 3%; in another embodiment, the concentration of HF is greater than 0% to less than about 5% by weight. The amount of HF added is sufficient to form a mixture, which can separate out the 244bb and to form a product which is substantially free of 1233xf and which is purer in the 244bb than the resulting mixture. In an embodiment, the resulting mixture is not a ternary azeotrope or ternary azeotropic-like composition. In another embodiment, the resulting mixture forms a ternary azeotrope or ternary azeotropic-like composition. The amount of HF present in the mixture is less than about 10 wt % of the mixture. In another embodiment, HF is present in less than about 5 wt % of the mixture. In still further embodiment, the amount of HF is present is less than about 3 wt % of the mixture. The resulting composition is distilled and the product substantially free of 1233xf is collected from the column reboiler and is fed forward to Step (3) reactor. A stream consisting of mainly 244bb/1233xf/HF exits the top of the column and is recycled back to the phase separator.

In Step (3) of the subject process to produce 1234yf, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g. SS 316), austenitic nickel-based alloys (e.g. Inconel 625), nickel, fluorinated 10% CsCl/MgO, and 10% CsCl/$MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

The following examples of the invention are not to be construed as limiting.

Example 1

This example illustrates the addition of HF into a mixture of 244bb, 1233xf, 1232zf, 243 isomer, and 1230xa dimers in separating 1233xf and other recyclable by-products in subsequent distillation. The distillation column used consisted of a 10 gallon reboiler, 2 inch ID by 8 feet Propack column, and a 5 ft² shell and tube condenser. The column is packed with Monel ¼" Pro-Pack dump packing and has about 30 theoretical plates. The distillation column is equipped with temperature, pressure, and differential pressure transmitters.

59.7 lbs of a mixture containing HF, 1233xf, 1232xf, 243, and some heavy components (boiling point higher than ~0.60° C.) are charged to the distillation column with 10 gallon reboiler. The mixture consists of 95% HF and 5% organic as indicated above. The column is brought into a total reflux. Temperature of the reboiler is ~36° C. and the column pressure is ~13 psig. The sample is then taken from the column overhead. The sample contains some HF as verified by pH measurement. The GC analysis of organic portion reveals 1.1% 244bb, 76.8% 1233xf, 3.4% 243, 13.9% 1232xf, and 4.8% of other compounds.

106 lbs of 3% HF/92.15%244bb/4.85%1233xf was charged into reboiler. Batch distillation was started at 40 psig. Samples were periodically taken from column overhead and reboiler and analyzed by GC for organic compositions and by acid-base titration for HF concentrations. Continuous distillation was initiated after 244bb concentration in the reboiler reached about 98 GC area % (or 1233xf was about 2 GC area %). The mixed feed comprising HF, 244bb, and 1233xf was continuously fed into column as a liquid form through a feeding port located in the middle of the column. The overhead stream was directed to a 10 wt % KOH aqueous solution for acid removal and then the organic was compressed and collected into a PCC (product collection cylinder) after being passed through a drying column. The reboiler stream was directly compressed and collected into another PCC. During the course of operation, the liquid level in reboiler was maintained at a constant level by keeping the sum of overhead takeoff rate and reboiler removal rate equal to the feed rate. As shown in Table 1, 1233xf was enriched in overhead stream but depleted in reboiler stream. As a result, 98 GC area % 244bb was obtained from the distillation. Analysis also indicated that almost all HF included in feed left distillation column from the overhead (in other words, no or little HF appeared in reboiler stream).

TABLE 1

| Time, h | Feed rate[1], lb/h | OH take-off rate, lb/h | Reboiler stream rate, lb/h | Composition at overhead stream, GC area % | | | | Composition at reboiler stream, GC area % | | | |
|---|---|---|---|---|---|---|---|---|---|---|---|
| | | | | 245cb | 244bb | 1233xf | others | 245cb | 244bb | 1233xf | others |
| 4 | 0.5 | 0.15 | 0.35 | 0.0349 | 92.1626 | 7.8025 | 0.0000 | | | | |
| 8 | 0.5 | 0.15 | 0.35 | 0.0102 | 92.5472 | 7.4335 | 0.0091 | | | | |
| 12 | 0.5 | 0.15 | 0.35 | | 92.5188 | 7.2292 | 0.2520 | | 98.0218 | 1.9630 | 0.0152 |
| 16 | 0.5 | 0.15 | 0.35 | 0.0063 | 91.9291 | 8.0579 | 0.0067 | | | | |
| 20 | 0.5 | 0.15 | 0.35 | 0.0075 | 91.8093 | 8.1832 | 0.0000 | | | | |

[1]Feed composition: 3 wt % HF/97 wt % organic (0.0029% 245cb, 94.9636% 244bb, and 5.0335% 1233xf)

Example 2

This example illustrates how the addition of HF into a mixture of 244bb and 1233xf helps remove 1233xf in subsequent distillation. The distillation column used consisted of a 10 gallon reboiler, 2 inch ID by 8 feet Propack column, and a 5 ft² shell and tube condenser. The column was packed with Monel ¼" Pro-Pack dump packing and had about 30-35 theoretical plates. The distillation column was equipped with temperature, pressure, and differential pressure transmitters.

Example 3

This distillation was conducted as in Example 2, using in the same distillation column except that a feed containing only about 400 ppm (about 0.04% by weight) of liquid HF was used. As shown in Table 2, with the presence of HF at just hundreds of ppm the 1233xf concentrations in the overhead takeoff stream were above 6 GC area % while they remained at around 2.5 GC area % in the reboiler drawoff stream, indicating the presence of HF even at just hundreds of ppm facilitates the separation of 1233xf from 244bb.

TABLE 2

| Time, h | Feed rate, lb/h | OH take-off rate, lb/h | Reboiler stream rate, lb/h | Composition at overhead stream, GC area % | | | | Composition at reboiler stream, GC area % | | | |
|---|---|---|---|---|---|---|---|---|---|---|---|
| | | | | 245cb | 244bb | 1233xf | others | 245cb | 244bb | 1233xf | others |
| 4 | 1.5 | 0.9 | 0.6 | | 93.6515 | 6.3485 | 0.0000 | | 97.5396 | 2.4604 | 0.0000 |
| 8 | 1.5 | 0.9 | 0.6 | | 93.6585 | 6.2925 | 0.0490 | | 97.5003 | 2.4997 | 0.0000 |
| 12 | 1.5 | 0.9 | 0.6 | | 94.2539 | 5.7461 | 0.0000 | | | | |
| 16 | 1.5 | 0.9 | 0.6 | | 93.9344 | 6.0656 | 0.0000 | | | | |
| 20 | 1.5 | 0.9 | 0.6 | | 93.7662 | 6.2338 | 0.0000 | | 97.4410 | 2.5434 | 0.0156 |
| 24 | 1.5 | 0.9 | 0.6 | | 93.8983 | 6.1017 | 0.0000 | | 97.4466 | 2.5534 | 0.0000 |
| 28 | 1.5 | 0.9 | 0.6 | | 93.7186 | 6.2814 | 0.0000 | | 97.4543 | 2.5457 | 0.0000 |
| 32 | 1.5 | 0.9 | 0.6 | | 93.8642 | 6.1358 | 0.0000 | | 97.4230 | 2.5770 | 0.0000 |
| 36 | 1.5 | 0.9 | 0.6 | | 93.8747 | 6.1253 | 0.0000 | | | | |
| 40 | 1.5 | 0.9 | 0.6 | | 93.6065 | 6.3935 | 0.0000 | | | | |

TABLE 2-continued

| Time, | Feed rate, lb/h | OH take-off rate, lb/h | Reboiler stream rate, lb/h | Composition at overhead stream, GC area % | | | | Composition at reboiler stream, GC area % | | | |
|---|---|---|---|---|---|---|---|---|---|---|---|
| | | | | 245cb | 244bb | 1233xf | others | 245cb | 244bb | 1233xf | others |
| 44 | 1.5 | 0.9 | 0.6 | | 93.7067 | 6.2933 | 0.0000 | | 97.4151 | 2.5849 | 0.0000 |
| 48 | 1.5 | 0.9 | 0.6 | | 93.7888 | 6.2112 | 0.0000 | | 97.3860 | 2.614 | 0.0000 |
| 52 | 1.5 | 0.9 | 0.6 | | 93.8067 | 6.1933 | 0.0000 | | | | |
| 56 | 1.5 | 0.9 | 0.6 | | 93.6921 | 6.3041 | 0.0038 | | | | |
| 60 | 1.5 | 0.9 | 0.6 | | 93.7278 | 6.2722 | 0.0000 | | 97.3845 | 2.6155 | 0.0000 |

[1]Feed composition: ~400 ppm HF/~99.96 wt % organic (94.9376% 244bb, and 5.0554% 1233xf)

What is claimed is:

1. A process to prepare 2-chloro-3,3,3-trifluoropropene (1233xf) comprising providing a starting composition comprising at least one starting compound of formula I, II or formula III:

$$CX_2=CCl-CH_2X \quad (I)$$

$$CX_3-CCl=CH_2 \quad (II)$$

$$CX_3-CHCl-CH_2X \quad (III)$$

wherein X is independently selected from the group consisting of F, Cl, Br, and I, provided that at least one X is not fluorine;
(a) contacting said starting composition with a fluorinating agent under conditions effective to produce a first composition comprising 1233xf, unreacted fluorinating agent, HCl, optionally unreacted starting compound, one or more organics selected from the group consisting of trichlorofluoropropene (1231) isomers, 2,3-dichloro-3,3-difluoropropene (1232xf), 1,1,1,2,2-pentafluoropropane (245cb), dichlorotrifluoropropane (243) isomers, trichlorodifluorpropane (242) isomers, and one or more dimers selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof;
(b) separating, from the first composition, a second composition comprised of an amount of 1233xf and substantially all of said organics and diners;
(c) providing said second composition to a distillation column and adding HF to the second composition in an amount effective to form a third composition comprising HF-azeotropes of 1233xf and at least one of the organics, such that binary and/or ternary azeotropic or azeotrope-like compositions of the organics with HF is formed, said second composition further comprising the dimers;
(d) separating the HF-azeotropes from the one or more dimers by distillation; and
(e) recovering 1233xf and one or more organics from the HF-azeotropes of step (d).

2. The process of claim 1 wherein the separation of step (b) is by phase separation.

3. A process to prepare 2,3,3,3-tetrafluoropropene (1234yf) comprising:
a) providing a first intermediate composition comprising 2-chloro-3,3,3-trifluoropropene (1233xf) as prepared according to claim 1;
b) contacting said first intermediate composition comprising 1233xf with a first concentration of HF in the presence of a fluorination catalyst under conditions effective to produce a second intermediate composition comprising 244bb; and
c) dehydrochlorinating at least a portion of said 244bb to produce a reaction product comprising 1234yf.

4. The process of claim 3 wherein the second intermediate composition further comprises unreacted 1233xf.

5. The process of claim 3 wherein a second concentration of HF is added to the second intermediate composition in an amount effective to form an azeotrope with the unreacted 1233xf.

6. The process of claim 5 wherein the azeotrope of the unreacted 1233xf is separated from the 244bb.

7. The process of claim 6 wherein the azeotrope of the unreacted 1233xf is separated from the 244bb by distillation.

8. The process of claim 6 wherein the unreacted 1233xf is recovered.

9. The process of claim 8 wherein the unreacted 1233xf is recycled to step (a).

10. The process of claim 5 wherein the HF is added in an amount of between about 0.01% to about 20% based on the weight of the second intermediate composition.

11. The process of claim 10 wherein the HF is added in an amount of between about 0.05% to about 10% based on the weight of the second intermediate composition.

12. A process to prepare 2,3,3,3-tetrafluoropropane (1234yf) comprising providing a starting composition comprising at least one starting compound of formula I, II or formula III:

$$CX_2=CCl-CH_2X \quad (I)$$

$$CX_3-CCl=CH_2 \quad (II)$$

$$CX_3-CHCl-CH_2X \quad (III)$$

wherein X is independently selected from the group consisting of F, Cl, Br, and I, provided that at least one X is not fluorine;
(a) contacting said starting composition with a fluorinating agent under conditions effective to produce a first composition comprising 1233xf, unreacted fluorinating agent, HCl, optionally unreacted starting compound, one or more organics selected from the group consisting of trichlorofluoropropene (1231) isomers, 2,3-dichloro-3,3-difluoropropene (1232xf), 1,1,1,2,2-pentafluoropropane (245cb), dichlorotrifluoropropane (243) isomers, trichlorodifluorpropane (242) isomers, and one or more dimers selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof;
(b) separating, from the first composition, a second composition comprised of an amount of 1233xf and substantially all of said organics and dinners;
(c) adding a first concentration of HF to the second composition in an amount effective to form a third composition comprising RF-azeotropes of 1233xf and at least one of the organics, said second composition further comprising the dimers;

(d) separating the HF-azeotropes from the dimers; and (e) recovering a first intermediate composition comprising 1233xf from the HF-azeotropes of step (d);

(f) contacting said first intermediate comprising 1233xf with a second concentration of HF in the presence of a fluorination catalyst under conditions effective to produce a second intermediate composition comprising 244bb; and (g) adding a third concentration of HF to the second intermediate composition in an amount effective to form an azeotrope with the unreacted 1233xf;

(h) dehydrochlorinating at least a portion of said 244bb to produce a reaction product comprising 1234yf.

13. The process of claim 12 wherein the azeotrope of the unreacted 1233xf is separated from the 244bb.

14. The process of claim 13 wherein the azeotrope of the unreacted 1233xf is separated from the 244bb by distillation.

15. The process of claim 13 wherein the unreacted 1233xf is recovered.

16. The process of claim 15 wherein the unreacted 1233xf is recycled to step (e).

17. The process of claim 12 wherein the third concentration of HF is added in an amount of between about 0.01% to about 20% based on the weight of the intermediate composition.

18. The process of claim 17 wherein the third concentration of HF is added in an amount of between about 0.05% to about 10% based on the weight of the intermediate composition.

* * * * *